United States Patent [19]

Trofimenko

[11] Patent Number: 5,097,000
[45] Date of Patent: Mar. 17, 1992

[54] 9,9-BIS (PERFLUOROALKYL) XANTHENE, 9-ARYL-9-PERFLUOROALKYLXANTHENE, MONOMERS AND POLYMERS DERIVED THEREFROM

[75] Inventor: Swiatoslaw Trofimenko, Wilmington, Del.

[73] Assignee: E. I. Du Pont de Nemours and Company, Wilmington, Del.

[21] Appl. No.: 718,936

[22] Filed: Jun. 21, 1991

Related U.S. Application Data

[62] Division of Ser. No. 527,740, May 23, 1990, Pat. No. 5,051,520.

[51] Int. Cl.$^5$ .............. C08G 63/00; C08G 73/10; C08G 69/20; C07D 311/82
[52] U.S. Cl. .................... 528/183; 528/125; 528/170; 528/172; 528/173; 528/176; 528/185; 528/188; 528/190; 528/191; 528/329.1; 528/350; 528/353; 549/388
[58] Field of Search .............. 528/183, 176, 185, 188, 528/190, 191, 125, 170, 172, 173, 350, 353, 329.1; 549/388, 241

[56] References Cited

U.S. PATENT DOCUMENTS

| 4,876,329 | 10/1989 | Chiang et al. | 528/353 |
| 4,912,197 | 3/1990 | Hayes | 528/353 |
| 4,997,908 | 3/1991 | Lee | 528/353 |
| 5,003,031 | 3/1991 | Schwartz et al. | 528/188 |
| 5,003,086 | 3/1991 | Stults et al. | 549/234 |
| 5,021,168 | 6/1991 | Molinaro et al. | 549/241 |

Primary Examiner—John Kight, III
Assistant Examiner—P. Hampton-Hightower

[57] ABSTRACT

Disclosed are rigid fluorinated monomers, their preparation, and polymers derived therefrom based on two novel tricyclic xanthene core systems, 9,9-bis-(perfluoroalkyl)xanthene (I) and 9-phenyl-9-perfluoroalkylxanthene (II). The monomers have utility in the preparation of advanced high-performance polymers, particularly polyimides.

8 Claims, No Drawings

9,9-BIS (PERFLUOROALKYL) XANTHENE, 9-ARYL-9-PERFLUOROALKYLXANTHENE, MONOMERS AND POLYMERS DERIVED THEREFROM

This is a division of application Ser. No. 07/527,740, filed May 23, 1990 now U.S. Pat. No. 5,051,520.

BACKGROUND OF THE INVENTION

The present invention relates to a new class of stiff, fluorinated, polycyclic xanthene monomers and polymers prepared therefrom.

The ever more stringent performance requirements of the electronic packaging industry mandate the development of polymers with lower dielectric constant and lower moisture absorption. Improvement in these properties has in the past been effected by the introduction of fluorine into the polymer. Unfortunately, this was always accompanied by deterioration of other properties, such as lowering of the glass transition temperature, increasing the coefficient of thermal expansion and increasing solvent sensitivity.

SUMMARY OF THE INVENTION

Accordingly, the present invention relates to a new class of stiff, fluorinated monomers, based on two novel tricyclic xanthene core systems, 9,9-bis(perfluoroalkyl)xanthene (I) and 9-phenyl-9-perfluoroalkylxanthene (II)

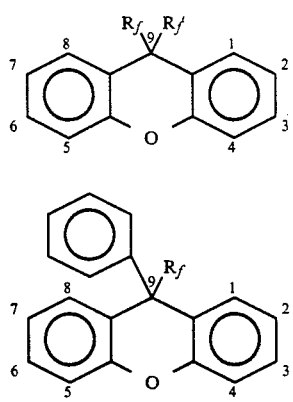

The monomers have utility in the preparation of advanced high-performance polymers, particularly polyimides. The rigid core decreases the coefficient of thermal expansion of the polymers while the fluorine substituents improve the dielectric constant and water absorption properties.

The novel invention compositions contain both a —CR$_f$R'$_f$— or —C(phenyl)R$_f$— bridge and a —O— bridge.

According to the present invention there is provided a composition of matter, and the preparation thereof, of the formula

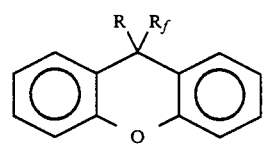

wherein R is selected from the group consisting of phenyl, substituted phenyl and perfluoroalkyl of 1 to 16 carbon atoms and R$_f$ is perfluoroalkyl of 1 to 16 carbon atoms.

In a further embodiment of the invention there is provided a composition of matter, and the preparation thereof, of the formula

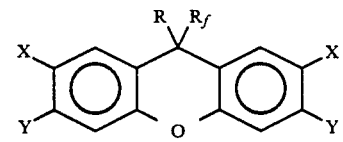

wherein R is selected from the group consisting of phenyl, substituted phenyl and perfluoroalkyl of 1 to 16 carbon atoms, 16 carbon atoms: R$_f$ is perfluoroalkyl of 1 to 16 carbon atoms; X is selected from the group consisting of H, CH$_3$, CO$_2$H, COCl, NH$_2$ and NCO; Y is the same as X; and X and Y together are —CO—O—CO—.

Another embodiment of the invention comprises a novel composition of the formula

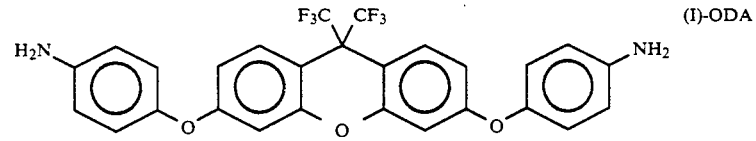

(I)-ODA

The invention further relates to a polyimide polymer having the following recurring structural unit

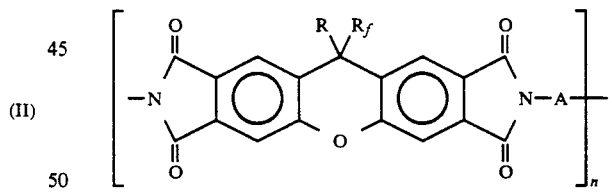

wherein R is selected from the group consisting of phenyl, substituted phenyl and perfluoroalkyl of 1 to 16 carbon atoms; R$_f$ is perfluoroalkyl of 1 to 16 carbon atoms; A is a divalent radical containing at least two carbon atoms, the two amino groups of said diamine each being attached to separate carbon atoms of said divalent radical; and n is a positive integer.

In the above definitions of R and R$_f$ as perfluoroalkyl, a more preferred number of carbon atoms is 1 to 18.

DETAILED DESCRIPTION OF THE INVENTION

The core ring systems (I) of the compositions of the invention can be prepared by using either a single-bridging or a double-bridging process. Scheme I depicts the preparation of 9,9-bis(trifluoromethyl)-2,3,6,7-tetramethylxanthene (III) using both processes.

In the double-bridging process both the ether bridge and the —C(CF₃)₂—bridge are introduced in a single step. This involves reaction of hexafluoroacetone (HFA) with two molar equivalents of 3,4-dimethylphenol to form the bridging —C(CF$_3$)$_2$—linkage concurrent with intramolecular dehydration of the two hydroxyl groups ortho to the —C(CF$_3$)$_2$—bridge to form the xanthene ether link of (III). The reaction is run in hydrofluoric acid (HF) at temperatures ranging from 180° to 220° C. using a molar ratio of HF/HFA of 10 or more.

Other substrates such as resorcinol and 3-aminophenol may be used in the simultaneous HFA bridging and cyclodehydration process. Reaction of resorcinol with two molar equivalents of HFA at 220° C. (Scheme II) provided 9,9-bis(trifluoromethyl)-3,6-dihydroxy xanthene (VII).

Reaction of (VII) with two equivalents of p-nitrochlorobenzene in dimethylacetamide solvent in the presence of potassium carbonate followed by hydrogenation of the dinitro precursor, provided 9,9-bis-(trifluoromethyl)-3,6-bis(4-aminophenoxy)-xanthene (VIII), a new diamine monomer for use in polymer synthesis. A polyester (IX) derived from reaction of (VII) with a mixture of isophthaloyl and terephthaloyl chlorides was also found to have utility as a high flux membrane film for $O_2/N_2$ separation.

The parent monomer, 9,9-bis(trifluoromethyl)-xanthene (I, $R_f=R'_f=CF_3$) was prepared by reaction of (VII) with sodium hydride and 5-chloro-1-phenyl-1H-tetrazole to form 9,9-bis(trifluoromethyl)-3,6-bis(1-phenyl-1H-tetrazolyl-5-oxy)xanthene which was catalytically reduced to (I) (Scheme IV).

SCHEME I

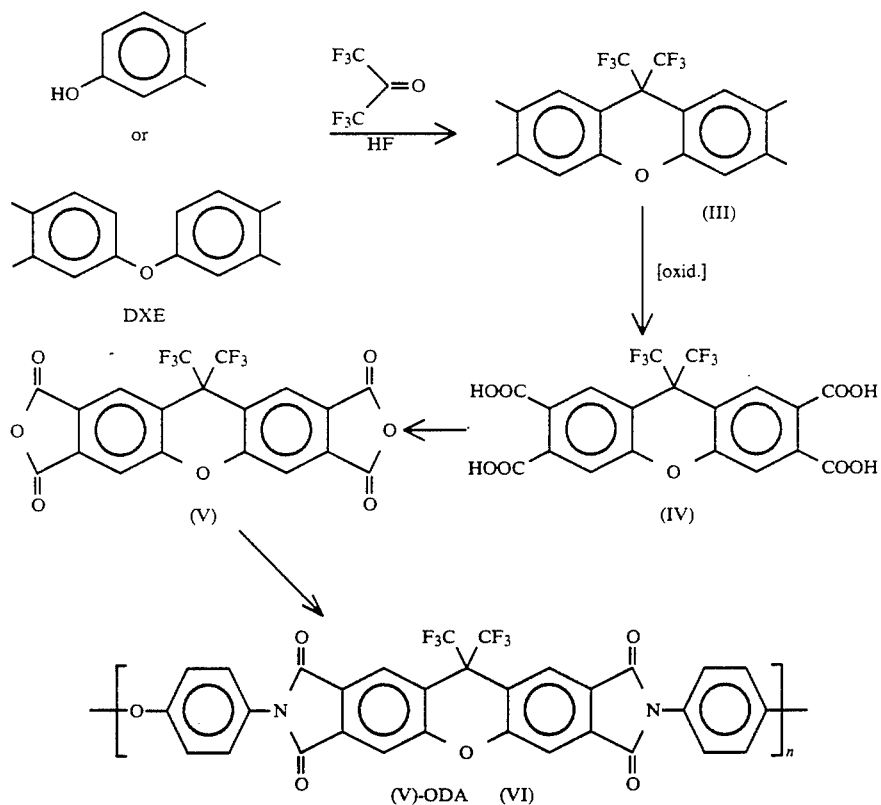

SCHEME II

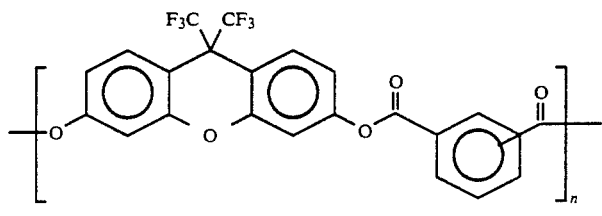

7:3 mixture of isophthaloyl and terephthaloyl links
(IX)

-continued

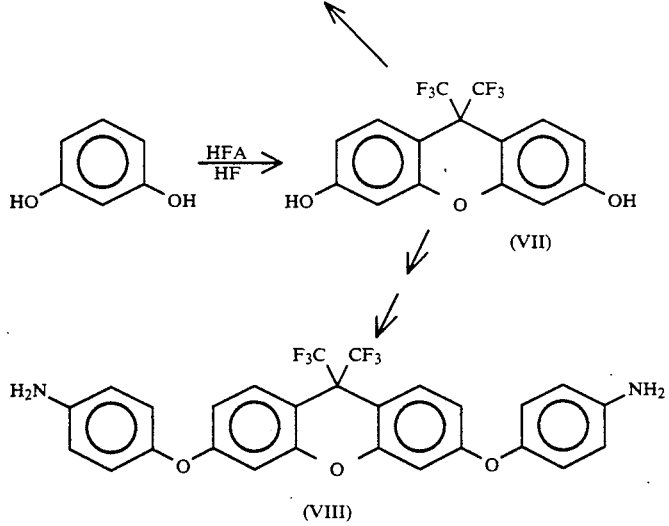

(VII)

(VIII)

SCHEME IV

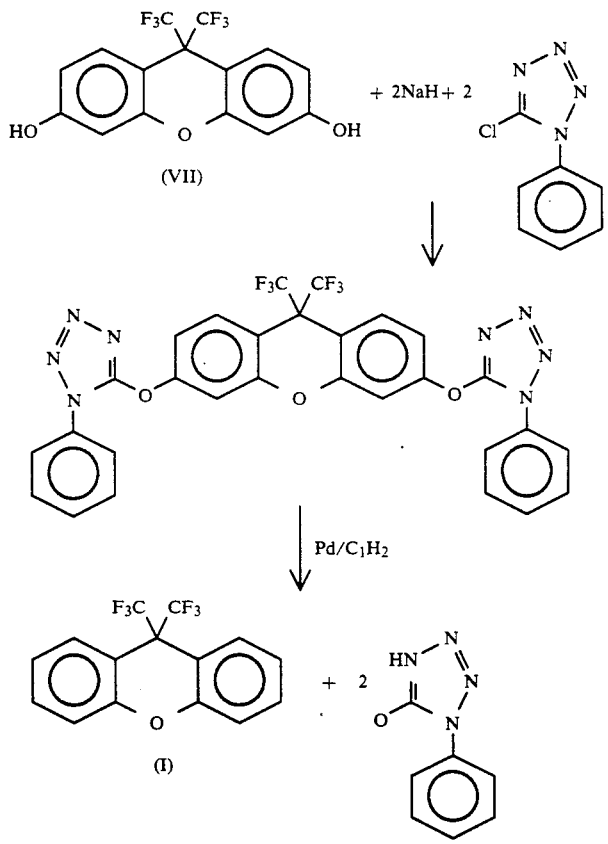

In the single-bridging process for preparing the core ring systems (Scheme I), the ether linkage is first performed separately followed by formation of the —C(CF$_3$)$_2$—bridge. Thus, (III) was prepared by reacting HFA in HF with 3,3'-di-o-xylyl ether (DXE), which already contained the xanthene ether linkage, at temperatures ranging from 110° to 140° C. and an HF/DXE ratio of 8–20, preferably 10–15.

The single-bridging process is preferred to the double-bridging process for preparing the core ring systems (I), since it requires lower reaction temperatures, gives higher yields despite being a two-step process, and generates fewer by-products.

Other aromatic ethers terminated by 3,4-dimethylphenoxy groups can also be used in the single-bridging process. For example, p-tolylether (Scheme III, X) reacts with HFA in HF to provide 9,9-bis-(trifluoromethyl)-2,7-dimethylxanthene (XI).

SCHEME III

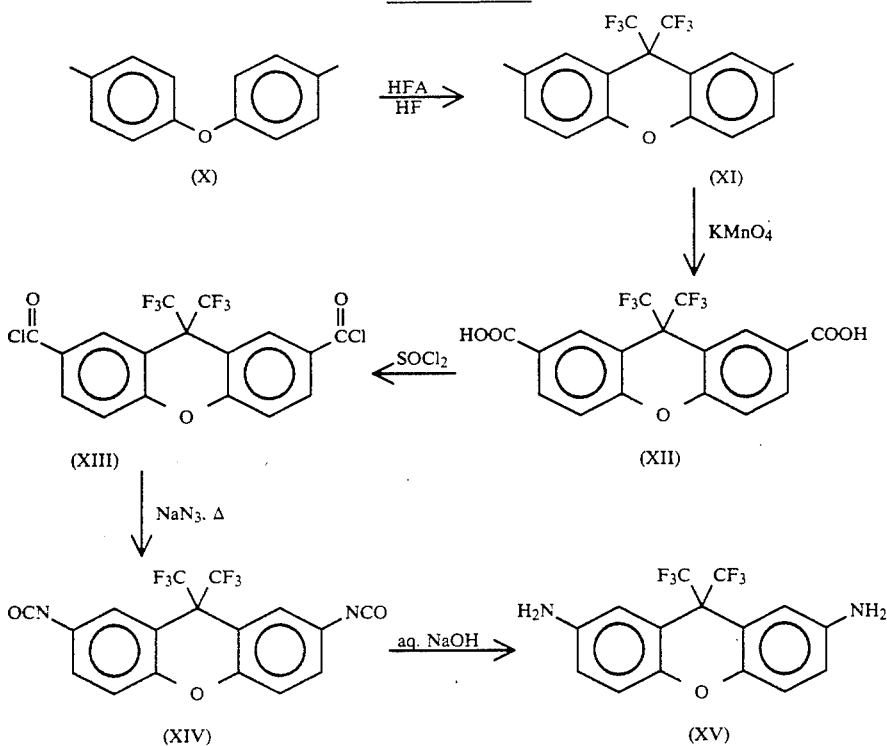

Once produced, (III) (Scheme I) was readily oxidized to 9,9-bis(trifluoromethyl)-2,3,6,7-xanthene-tetracarboxylic acid (IV), dehydrated to 9,9-bis-(trifluoromethyl)xanthene tetracarboxylic dianhydride (V) and subsequently polymerized with 4,4'-diaminodiphenylether to form polyimide (VI) (V-ODA). Analogous polyimides were obtained using 3,4'-diaminodiphenylether, (I)-ODA and paraphenylenediamine.

Oxidation of (III) to the tetraacid (IV) was performed using potassium permanganate in aqueous pyridine. Other methods, such as Mn/Co catalyzed oxidation with oxygen or air, or oxidation with nitric acid can also be used.

Conversion of (IV) to the dianhydride (V) can be effected thermally, by boiling in acetic anhydride, or by heating a slurry of (IV) in chloroform with excess thionyl chloride. Thermal conversion by heating at 220° C. overnight is preferred. The polyimide (VI) was prepared by reacting the dianhydride (V) with a substantially equimolar amount of 4,4'-diaminodiphenylether in dimethylacetamide to form a polyamide acid and then thermally converting the polyamide acid to the polyimide.

In similar fashion (XI) (Scheme III) was oxidized with permanganate to 9,9-bis(trifluoromethyl)xanthene-2,7-dicarboxylic acid (XII) and then reacted with thionyl chloride to provide 9,9-bis(trifluoromethyl)-xanthene-2,7-dicarbonyl chloride (XIII). The diacid chloride was subsequently reacted with sodium azide by the Curtius Reaction to provide 9,9-bis(trifluoromethyl)xanthene-2,7-diisocyanate (XIV) which was hydrolyzed to 9,9-bis(trifluoromethyl)xanthene-2,7-diamine (XV).

The core ring system (II) was prepared in similar fashion using the single-bridging process and RCOR$_f$ instead of HFA to provide analogous compounds

SCHEME V

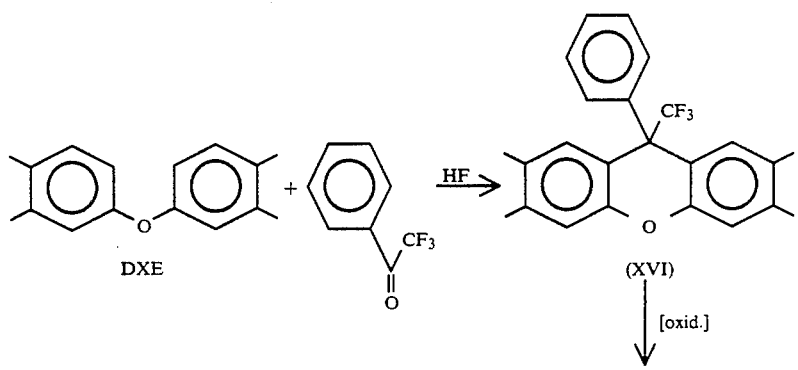

-continued

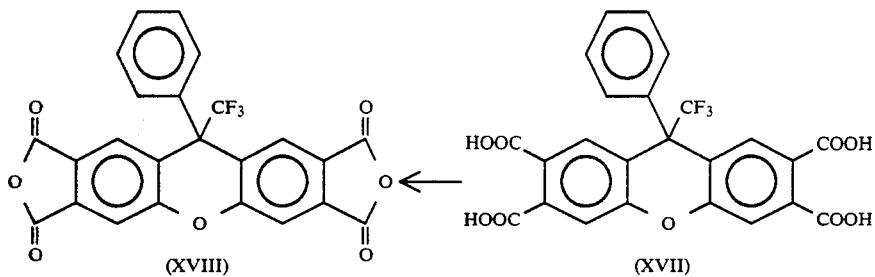

SCHEME VI

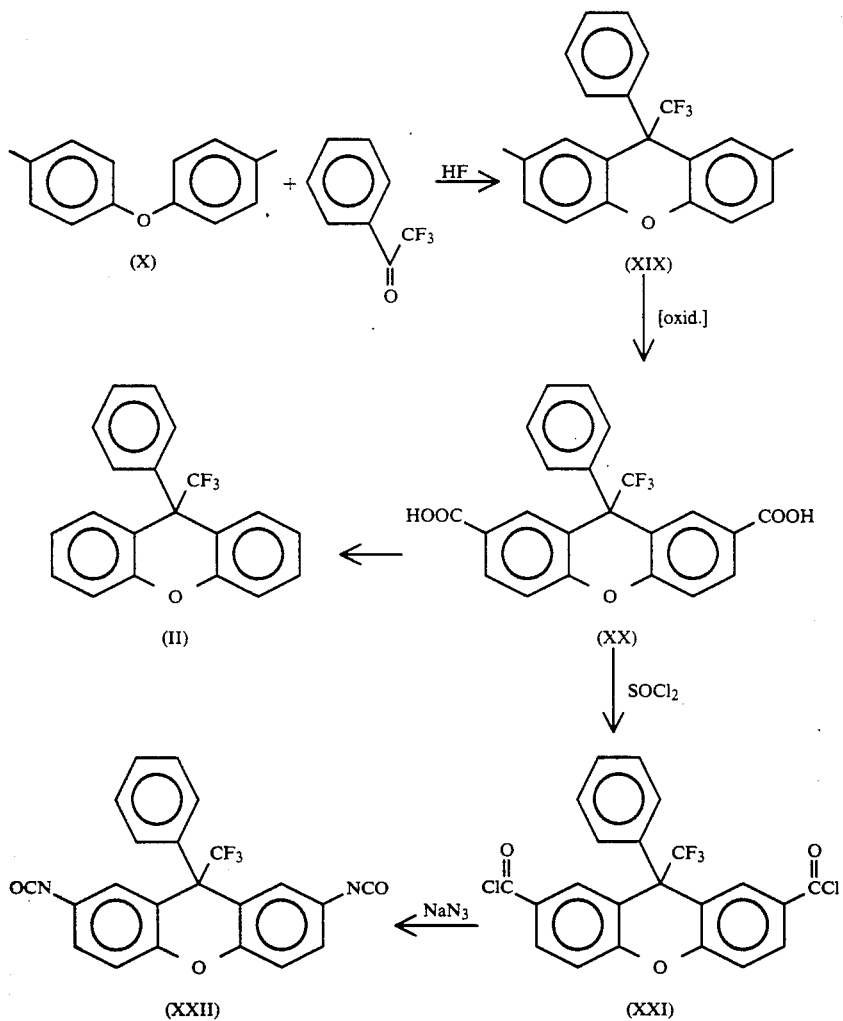

containing a —CRR$_f$— bridge instead of a —C(CF$_3$)$_2$— bridge. Compounds of the structure RCOR$_f$ include those wherein R is phenyl or substituted phenyl and R$_f$ is CF$_3$, C$_2$F$_5$, C$_3$F$_7$ and C$_8$F$_{17}$.

For example, the reaction of 3,3'-di-o-xylyl ether (DXE) with trifluoroacetylbenzene (R=phenyl, R$_f$=CF$_3$) in HF at 140° C. provided 9-phenyl-9-trifluoromethyl-2,3,6,7-tetramethylxanthene (XVI) (Scheme V). Oxidation of (XVI) with potassium permanganate gave 9-phenyl-9-(trifluoromethyl)xanthene-2,3,6,7-tetracarboxylic acid (XVII) which was thermally converted to 9-phenyl-9-trifluoromethyl)xanthene-2,3,6,7-tetracarboxylic dianhydride (XVIII) by heating under vacuum at 250° C.

The parent monomer (II, R$_f$=CF$_3$) was prepared (Scheme VI) using the single-bridging process by reaction of p-tolyl ether (X) and trifluoromethylphenyl ketone in HF at 130° C. to provide 9-phenyl-9-trifluoromethyl-2,7-dimethylxanthene (XIX), followed by oxidation to the dicarboxylic acid (XX) and catalytic decarboxylation to (II). The diacid (XX) could also be converted to the diacyl chloride (XXI), then to the diacyl azide and, finally, to the diisocyanate (XXII) as previously described.

Polyimides encompassed by the present invention include those having the recurring structural unit

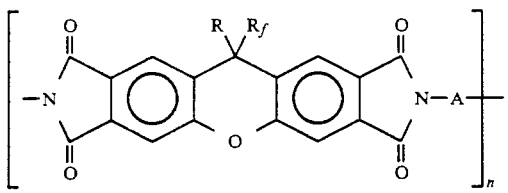

wherein R is selected from the group consisting of phenyl, subtituted phenyl and perfluoroalkyl of 1 to 16 carbon atoms; $R_f$ is perfluoroalkyl of 1 to 16 carbon atoms (and more preferably 1 to 8 carbon atoms); A is a divalent radical containing at least two carbon atoms, the two amino groups of said diamine each being attached to separate carbon atoms of said divalent radical and n is a positive integer.

The polyimides display outstanding physical properties making them useful as shaped structures such as self-supporting films, fibers and filaments. The structures are characterized by high tensile properties, desirable electrical properties, stability to heat and water and very low coefficient of thermal expansion.

The polyimides are generally prepared by reacting dianhydrides (V) or (XVIII) with an aromatic diamine in an inert organic solvent to form a polyamide acid solution and subsquently converting the polyamide-acid to polyimide essentially as described in U.S. Pat. Nos. 3,179,614; 3,179,630 and 3,179,634, the disclosures of which are incorporated herein by reference.

If desired, dianhydrides (V) or (XVIII) can also be blended with from 15 to 85 mole % of other dianhydrides, such as pyromellitic dianhydride; 2,3,6,7-naphthalene tetracarboxylic dianhydride; 3,3',4,4'-biphenyl tetracarboxylic dianhydride; 1,2,5,6-naphthalene tetracarboxylic dianhydride; 2,2',3,3'-biphenyl tetracarboxylic dianhydride; 3,3',4,4'-benzophenone tetracarboxylic dianhydride; 2,2-bis(3,4-dicarboxyphenyl) propane dianhydride; bis(3,4-dicarboxyphenyl) sulfone dianhydride; 3,4,9,10-perylene tetracarboxylic dianhydride; bis(3,4-dicarboxyphenyl) propane dianhydride; 1,1-bis-(2,3-dicarboxyphenyl) ethane dianhydride; 1,1-bis-(3,4-dicarboxyphenyl) ethane dianhydride; bis-(2,3-dicarboxyphenyl) methane dianhydride; bis-(3,4-dicarboxyphenyl) methane dianhydride; oxydiphthalic dianhydride; bis (3,4-dicarboxyphenyl) sulfone dianhydride; and the like.

Suitable diamines for use in the polyimide compositions of the invention include:
meta-phenylenediamine;
paraphenylene diamine;
4,4'-diamino-diphenyl propane;
4,4'-diamino-diphenyl methane;
benzidine;
4,4'-diamino-diphenyl sulfide;
4,4'-diamino-diphenyl sulfone;
3,3'-diamino-diphenyl sulfone;
4,4'-diamino-diphenyl ether;
2,6-diamino-pyridine;
bis-(4-amino-phenyl)diethyl silane;
bis-(4-amino-phenyl)phosphine oxide;
bis-(4-amino-phenyl)-N-methylamine;
1,5-diamino-naphthalene;
3,3'-dimethyl-4,4'-diamino-biphenyl;
3,3'-dimethoxy benzidine;
2,4-bis(beta-amino-t-butyl)toluene;
bis-(para-beta-amino-t-butyl-phenyl)ether;
para-bis(2-methyl-4-amino-pentyl)benzene;
para-bis-(1,1-dimethyl-5-amino-pentyl)benzene;
m-xylylene diamine;
p-xylylene diamine;
bis(para-amino-cyclohexyl)methane;
hexamethylene diamine;
heptamethylene diamine;
octamethylene diamine;
nonamethylene diamine;
decamethylene diamine;
3-methylheptamethylene diamine;
4,4-dimethylheptamethylene diamine;
2,11-diamino-dodecane;
1,2-bis-(3-amino-propoxy)ethane;
2,2-dimethyl propylene diamine;
3-methoxy-hexamethylene diamine;
2,5-dimethylhexamethylene diamine;
2,5-dimethylheptamethylene diamine;
5-methylnonamethylene diamine;
1,4-diamino-cyclohexane;
1,12-diamino octadecane;
$H_2N(CH_2)_3O(CH_2)_3NH_2$;
$H_2N(CH_2)_3S(CH_2)_3NH_2$;
$H_2N(CH_2)_3N(CH_3)(CH_2)_3NH_2$;
and mixtures thereof.

Useful solvents include normally liquid N,N-dialkylcarboxylamides, generally. Preferred solvents include the lower molecular weight members of such carboxylamides, particularly N,N-dimethylformamide and N,N-dimethylacetamide. Other useful compounds of this class of solvents are N,N-diethylformamide and N,N-diethylacetamide. Other solvents which may be used are dimethylsulfoxide, N-methyl-2-pyrrolidone, tetramethyl urea, dimethylsulfone, hexamethylphosphoramide, tetramethylene sulfone, and the like. The solvents can be used alone, in combinations with one another or in combinations with poor solvents such as benzene, benzonitrile, dioxane, etc. The amount of solvent used preferably ranges from 75 to 90 weight % of the polyamic acid, since this concentration has been found to give optimum molecular weight.

Conversion of the polyamic acid to polyimide can be accomplished by either a thermal conversion or a chemical conversion process. According to the thermal conversion process, the polyamic acid solution is cast on a heated conversion surface, such as a metal drum or belt, and heated at a temperature of above about 50° C. to partially convert the polyamic acid to polyimide. The extent of polyamic acid conversion depends on the temperature employed and the time of exposure, but, generally about 25 to 95% of amic acid groups are converted to imide groups. The partially converted polyamic acid is then heated at or above 220° C. to obtain complete conversion to the polyimide.

In the chemical conversion process, the polyamic acid solution is first chilled to about 10° C. to −10° C. and polyamic acid conversion chemicals are added. The polyamic acid conversion chemicals are tertiary amine catalysts and anhydride dehydrating materials. The preferred anhydride dehydrating material is acetic anhydride and is used in slight molar excess of the amount of amic acid groups in the polyamic acid, typically about 2-2.5 moles per equivalent of polyamic acid. A comparable amount of tertiary amine catalyst is used. Besides acetic anhydride, other operable lower fatty acid anhydrides include propionic, butyric, valeric, mixed anhydrides of these with one another and with anhydrides of aromatic monocarboxylic acids, for example, benzoic acid, naphthoic acid, and the like, and with anhydrides of carbonic and formic acids, as well as aliphatic ketenes (ketene and dimethyl ketene). Ketenes may be regarded as anhydrides of carboxylic acids derived from drastic dehydration of the acids.

The preferred tertiary amine catalysts are pyridine and beta-picoline and they are used in an amount of about one mole per mole of anhydride dehydrating material. Tertiary amines having approximately the same activity as the preferred pyridine and beta-picoline may also be used. These include 3,4-lutidine; 3,5-lutidine; 4-methylpyridine; 4-isopropyl pyridine; N-dimethylbenzylamine; isoquinoline; 4-benzylpyridine; and N-dimethyldodecylamine. Trimethylamine and triethylamine are more active than those amines listed above and can be used in smaller amounts.

The polyamic acid conversion chemicals react at about room temperature or above to convert polyamic acid to polyimide. The chemical conversion reaction occurs at temperatures from 10° to 120° C., with the reaction being very rapid at the higher temperatures and very slow at the lower temperatures. Below a certain temperature, polyamic acid chemical conversion comes to a practical halt. This temperature is generally about 10° C. It is important, therefore, that the polyamic acid solution be chilled below this temperature before adding the polyamic acid conversion chemicals and that the temperature of the solution, with conversion chemicals, be maintained below this temperature during extrusion or casting.

The treated, chilled, polyamic acid solution is cast or extruded onto a heated conversion surface whereupon some of the solvent is evaporated from the solution, the polyamic acid is partially chemically converted to polyimide, and the solution takes the form of a polyamic acid-polyimide gel. Conversion of amic acid groups to imide groups depends on contact time and temperature but is usually about 25 to 95% complete.

The gel is subsequently dried to remove the water, residual solvent, and remaining conversion chemicals, and the polyamic acid is completely converted to polyimide. The drying can be conducted at relatively mild conditions without complete conversion of polyamic acid to polyimide at that time, or the drying and conversion can be conducted at the same time using higher temperatures. Preferably, high temperatures are used for short times to dry the film and convert it to polyimide in the same step. It is preferred to heat the film to a temperature of 200°–450° C. for 15 to 400 seconds.

The xanthene core monomers (I) and (II) are particularly useful for the preparation of polyimide polymers. The diacid chlorides, diacids, diisocyanates and diamine monomers of the present invention can also be used to prepare polyamides, polyesters, polycarbonates and polyurethanes by techniques which are well-known in the art.

The advantageous properties of this invention can be observed by reference to the following examples which illustrate, but do not limit, the invention. All parts and percentages are by weight unless otherwise indicated.

All reagents used were commercial materials, unless otherwise indicated. IR spectra were measured as Nujol mulls, or as polyimide films, on a Perkin-Elmer Grating IR Spectrophotometer Model 457. NMR spectra were determined on the GE QE-300 instrument, using deuterochloroform as solvent and tetramethylsilane as internal standard.

Aromatic Ether Precursors

All aryl ethers were prepared by the reaction of the appropriate potassium aryloxide with a mono- or dibromoaryl precursor, using NMP as solvent. The method is illustrated by the preparation of 3,3'-di-o-xylyl ether (DXE).

3,3'-di-o-xylyl Ether (DXE)

In a 3-L four-neck flask was placed 1.2 L toluene, 500 g (4.1 mole) of 3,4-dimethylphenol, and 227 g (4.1 mole) KOH pellets. The mixture was stirred with an efficient mechanical stirrer and refluxed, water being removed via a Dean-Stark trap. When all the water was removed, at which point the potassium phenolate salt started to crystallize out, about 500 ml toluene was distilled out (leaving enough toluene, so that the slurry was still stirrable). About 500 ml N-methylpyrrolidone (NMP) was added, along with 750 g (4.1 mole) 4-bromo-o-xylene, and 100 g copper powder. The reaction mixture was heated again, and remaining toluene was distilled out through a tall Vigreux column. When all the toluene had been distilled out, and the temperature in the flask reached about 200° C., the distillation column was replaced with a condenser, and the vigorously stirred mixture was refluxed overnight. The mixture was filtered through a bed of Celite, and the flask was rinsed with some DMF, which was used to wash the filter cake. The filtrate was concentrated at atmospheric pressure, until DMF and most of the NMP was distilled out, then distillation was continued at reduced pressure, collecting the product boiling at 140°–145° C./1.4–1.7 Torr. The still warm fraction was poured into 500 ml stirred methanol; this resulted in precipitation of a crystalline product, which was filtered off and washed with methanol. A second crop was obtained from the filtrate for a total yield in the 360–420 g (55–65%) range, taking into consideration that the starting 4-bromo-o-xylene was only 70% pure. NMR of the title material: d 7.03, d 6.80, dd 6.73, s 2.19 in the correct 1:1:1:6 ratio; the two non-identical methyl groups show up as a singlet. From the filtrates one could distill a fraction boiling where the main product boiled. This oil could not be crystallized, and by NMR consisted of an approximately 50/50 mixture of DXE and the mixed ether arising from the isomeric 3-bromo-o-xylene, which comprised almost 30% of the starting material.

Di-p-tolyl Ether (X)

Obtained in 56% yield; NMR: d 7.10, d 6.87, s 2.30 ppm in 2:2:3 ratio.

EXAMPLE 1

9,9-Bis(trifluoromethyl)xanthene (I, $R_f=R'_f=CF_3$)

A.
9,9-bis(trifluoromethyl)-3,6-bis(1-phenyl)-1H-tetrazolyl-5-oxy)xanthene

In 250 ml of dry diglyme was stirred at room temperature 5 g of 50% sodium hydride in mineral oil, plus 17.5 g (0.05 mole) 9,9-bis(trifluoromethyl)-3,6-dihydroxyxanthene (VII). The hydrogen evolved was measured by a wet-test meter. When hydrogen evolution stopped, 18.1 q (0.1 mole) of 5-chloro-1-phenyl-1H-tetrazole was added in one portion, and the mixture was stirred and gently heated until the second evolution of hydrogen stopped. The flask contents were drowned with stirring in 2.5 L ice water. A solid separated, which was filtered off, dissolved in methylene chloride, and filtered through a bed of alumina. The filtrate was stripped to dryness, and the residue was stirred with methanol, and was filtered. There was obtained a total of 27.1 g (86%) of a solid with a sharp IR spectrum, which contained no OH or CO peaks. The NMR spectrum was consistent with the assigned structure: d 7.97, dd 7.78, m 7.6, d 7.45, dd 7.34 in 1:2:3:1:1 ratio, assigned to the 1H, phenyl ortho H's, phenyl m and p H's, 4H, and 2H, respectively.

B. 9,9-bis(trifluoromethyl)xanthene (I)

A mixture of 25 g 9,9-bis(trifluoromethyl)-3,6-bis-(1-phenyl-1H-tetrazolyl-5-oxy)xanthene and 6 g of 5% palladium on carbon in 250 ml THF was heated in a shaker tube at 400 psi of hydrogen for 16 hrs at 100°. The pressure dropped by 42 psi which occurred within the first 9 hrs, and did not change thereafter. The reaction mixture was filtered, and the residue was fractionally distilled. The product distilled at 105°/1.2 Torr and was obtained in 5.0 g (39%) yield. It was recrystallized from methanol and purified further by vacuum sublimation. M.p. 74°–75° C. NMR: dd 7.88; td 7.44 plus overlapping td and dd 7.3–7.4 in 1:1:1:1 ratio; $C^{13}$ NMR: m 52.5 (bridgehead C), 110.0 (C next to the bridge), 117.6 (4C), 123.3 (2C), quartet (J=287 Hz) 124.3 ($CF_3$), 130.2 (1C), 131.5 (3C) and 151.0 (C next to O) ppm, in agreement with the assigned structure. The mass spectrum of (I) showed the molecular formula to be $C_{15}H_8F_6O$, and had a parent peak at 318, plus prominent peaks at 249 (parent minus $CF_3$), 199 (parent minus $C_2H_5$), 100 ($C_2F_4$) and 69 ($CF_3$). Elemental analysis: Calc. for $C_{15}H_8F_6O$: C 56.5; H 2.52; Found: C 56.6; H 2.91.

EXAMPLE 2

9-Phenyl-9-trifluoromethylxanthene (II, $R_f=CF_3$)

A 6 g sample of 9-phenyl-9-trifluoromethylxanthene-2,7-dicarboxylic acid (XX) was stirred and refluxed in 100 ml quinoline along with 11 g of copper powder, the emanating gas being measured by a wet-test meter. The theoretical amount of $CO_2$ was evolved in two hours. The reaction mixture was cooled, filtered through a bed of Celite into 800 ml of water, acidified with 100 ml of concentrated hydrochloric acid, and left standing overnight. The supernatant liquid was decanted, and the residue was taken up in methylene chloride, and filtered through a bed of alumina. The solvent was stripped, the residue was stirred with methanol, and was filtered, yielding 3.1 g (66%) of a white solid. It was recrystallized from methanol; m.p. 89°–90°. The IR spectrum was sharp with no OH or CO bands. The NMR spectrum was confirmatory, with the following peaks: d 7.42; m 7.3–7.4; d 7.19, td 6.96, d 6.87 in 2:5:2:2:2 ratio. The compound was analyzed by mass spectrometry which showed the parent ion at 326, along with other peaks, the strongest being at 257 (parent minus trifluoromethyl), and also at 249 (parent minus phenyl), and 199 (parent minus phenyl and minus difluorocarbene). The mass spectrum confirmed the molecular formula as $C_{20}H_{13}F_3O$.

EXAMPLE 3

9,9-Bis(trifluoromethyl)-2,3,6,7-tetramethylxanthene (III)

Double Bridging Process

A mixture of 330 g (2.7 moles) 3,4-dimethylphenol, 225 g (1.35 moles) HFA and 300 g (15 moles) HF was shaken in an autoclave for 15 hrs at 220°. The reaction mixture was poured into a one-gallon polyethylene jar, half-filled with ice-water and containing excess sodium hydroxide. The product was extracted with methylene chloride, the extracts were filtered through alumina, and stripped. Distillation of the residue in vacuo gave several fractions. The fraction, boiling at 190°–210°/1 Torr was chromatographed on alumina, packing and eluting with methylene chloride. The orange band was collected, and the fraction was stripped. Stirring of the residue with excess methanol, filtration, washing of the solid with more methanol, and air-drying gave 86 g (17%) of (III) which melts at 214°–215°, and sublimes readily in vacuo at 180°/1 Torr; it can be recrystallized from toluene or heptane, but is sparingly soluble in methanol. Analysis: Calc. for $C_{19}H_{16}F_6O$: C, 61.0; H, 4.28; F, 30.5; Found: C, 61.3, H, 4.40; F, 30.7% NMR: s 7.57, s, 6.95, s, 2.26 ppm in 1:1:6 ratio.

Single-Bridging Process

A mixture Of 200 g (0.88 mole) DXE, 150 g (0.88 mole) HFA, and 236 g (11.8 moles) HF was heated at 120° for 8 hrs in a shaker tube. After venting excess HF, the tube contents were drowned in a one-gallon polyethylene jar containing 2 L ice-water, and 500 ml of 50% NaOH. The shaker tube was rinsed out with methylene chloride, and the washings were added to the jar. Most of the aqueous layer was decanted, and the product was extracted wth 3–4 L of methylene chloride. The slurry was filtered once through a bed of Celite to remove a pasty sludge and the layers were separated. The organic layer was filtered through a layer of alumina, and then stripped to dryness. The reddish crystalline residue was dissolved in 150–200 ml of boiling toluene, partially cooled and diluted with 500 ml methanol, which resulted in rapid crystallization. The solid was filtered, washed with methanol until the washings were no longer red, and was air-dried, yielding 95–105 g (29–32%) of pale creamy solid. The filtrates were stripped to dryness, and the residue was distilled over a short-path column. Pale orange material boiling at 200°–210°/1 Torr was collected, dissolved in minimum quantity of boiling toluene and diluted with methanol, yielding another 15–20 g of product, for a total yield in the 33–41% range.

EXAMPLE 4

9,9-Bis(trifluoromethyl)-2,3,6,7-xanthenetetracarboxylic acid (IV)

9,9-Bis(trifluoromethyl-2,3,6,7-tetramethylxanthene (III) (20 g, 0.053 mole) was reluxed in a mixture of 400 ml pyridine and 200 ml water with rapid mechanical stirring, and 50 g (0.316 mole) potassium permanganate was added in portions through the top of the condenser. After addition was complete, the slurry was refluxed for 1 hr. The mixture was filtered hot through Celite, and concentrated down to about 50 ml. A mixture of 35 g NaOH and 535 ml water was added, and the oxidation was repeated, using 45 g (0.28 mole) $KMnO_4$. After the second oxidation, excess permanganate was destroyed with isopropyl alcohol. The mixture was filtered through Celite, and the filtrate was acidified with sulfuric acid. This produced a white precipitate, which was filtered, and washed thoroughly with water. The tetraacid (IV) was dried in a convection oven overnight at 150° and was obtained in 16 g yield (61%) It was used for conversion to the anhydride, without further purification.

EXAMPLE 5

9,9-Bis(trifluoromethyl)-xanthenetetracarboxylic Dianhydride (V)

9,9-Bis(trifluoromethyl)-2,3,6,7-xanthenetetracarboxylic acid (IV) was converted to dianhydride (V) by drying overnight in a convection oven at 220°. Even during drying at 150°–180° some conversion to the anhydride took place. The dehydration could be followed by means of changes in the carbonyl region from those of tetraacid (IV) (descending pattern at 1860, 1780, 1740 and 1710 cm$^{-1}$) to those of dianhydride (V) (1860, 1775 vs). Both, TGA and DSC data for (IV) indicate dehydration occurring around 240°, and the second event (melting/sublimation of (V)) taking place around 355°–360°.

Tetraacid (IV) could also be dehydrated by acetic anhydride; refluxing with excess acetic anhydride for one hour usually sufficed to dehydrate (IV). Dianhydride (V) was essentially insoluble in acetic anhydride, and could be isolated by simple filtration and drying of the slurry.

Another method, used for dehydrating tetraacid (IV) involved refluxing a slurry of (IV) in chloroform with excess thionyl chloride for two hours. Again, since dianhydride (V) was essentially insoluble in chloroform, simple filtration and washing with chloroform yielded the product.

Purification of dianhydride (V) could not be achieved by recrystallization since it has very low solubility in acetic acid/acetic anhydride mixtures. It could, however, be sublimed at 250°/1 Torr. This was done conveniently in small sublimer tubes, where fairly large crystals with a slight yellowish cast could be grown. Pure dianhydride (V) melts in a capillary at 355°–356°. IR (Nujol mull): 1860, 17775 (vs) cm$^{-1}$. It was too insoluble for determining its NMR spectrum. Analysis: Calc. for C$_{19}$H$_4$F$_6$O$_7$: C, 49.8; H, 0.87; F, 24.9; Found: C, 50.1; H, 1.11; F, 24.9%.

EXAMPLE 6

Polyimide films derived from 9,9-bis(trifluoromethyl)-xanthene tetracarboxylic dianhydride (V)

In a flame-dried and nitrogen-flushed 500 ml round-bottom flask was placed 5.00 g (0.025 mole) of 4,4'-diaminodiphenylether (ODA) which was dissolved in 200 ml dry NMP. To the stirred solution was added in portions 11.45 g (0.025 mole) of 9,9-bis(trifluoromethyl)-xanthenetetracarboxylic dianhydride (V). Most of the dianhydride (V) dissolved within one hour, but the rest only upon stirring overnight. Dianhydride (V) was doubly sublimed, but still not very pure, as it contained sublimation residue particles which adhered to the sublimate electrostatically. The 8% by weight solution of polyamic acid was converted into a film by either casting or spin coating, and cured at 350°–400° C. in air. The (V)-ODA film was very thin, but did have a sharp IR, and was characterized by imide peaks at 1785 and 1730 (vs) cm$^{-1}$.

More concentrated solutions, up to 27% solids, were prepared as above, and produced thicker (V)-ODA films with the properties listed in Table I.

In similar fashion, polyimide films were prepared from 9,9-bis(trifluoromethyl)xanthenetetracarboxylic dianhydride (V) and paraphenylenediamine (PPD), 3,4'-diaminodiphenyl ether (3,4'-ODA), resorcinol oxydianiline (RODA) and (I)-ODA. Physical properties of the films are given in Table I.

TABLE I

PHYSICAL PROPERTIES OF POLYIMIDE FILMS FROM 9,9-BIS (TRIFLUOROMETHYL) XANTHENE TETRACARBOXYLIC DIANHYDRIDE (V)

| Film | Spin or Cast | Final Temp. (°C.) | Cure Time (min.) | Thickness* (um) | Tensile Strength (MPa) | Elastic Modulus (GPa) | Elongation. (%) |
|---|---|---|---|---|---|---|---|
| (V)-ODA | Spin | 350 | 60 | 10 | 115 ± 8 | 1.6 ± 0.1 | 20 ± 6 |
|  | Spin | 350 | 60 | 23 ± 2 | 110 ± 6 | 1.5 ± 0.2 | 20 ± 6 |
|  | Cast | 350 | 60 | 6 ± 1 | 115 ± 9 | 1.3 ± 0.1 | 21 ± 6 |
|  | Cast | 350 | 60 | 18 ± 2 | 97 ± 5 | 1.2 ± 0.1 | 15 ± 2 |
|  | Cast | 350 | 60 | 27 ± 1 | 82 ± 18 | 1.8 ± 0.1 | 6 ± 3 |
| (V)-3,4'-ODA | Spin | 350 | 60 | 10 | 83 ± 6 | 1.4 ± 0.1 | 8 ± 1 |
| (V)-PPD | Spin | 350 | 60 | 8 | 147 ± 10 | 4.3 ± 0.2 | 4 |
|  | Spin | 350 | 60 | 47 ± 7 | 208 ± 21 | 4.0 ± 0.2 | 10 ± 1 |
|  | Spin | 400 | 60 | 8.3 ± 0.3 | 280 ± 21 | 7.1 ± 0.3 | 7 ± 2 |
| (V)-RODA | Spin | 400 | 60 | 6.5 ± 0.7 | 110 ± 19 | 2.3 ± 0.2 | 7 ± 3 |
| (V)-(I)ODA | Spin | 40 | 60 | 8.2 ± 0.3 | 126 ± 15 | 2.2 ± 0.2 | 16 ± 8 |

*Typical thickness deviations for cast films were ± 8 to 12%; for spin coated films ± 0.5 to 2%

EXAMPLE 7

9,9-Bis(trifluoromethyl)-2,7-dimethylxanthene (XI)

A mixture of 200 g (1 mole) p-tolyl ether, 1 66 g (1 mole) HFA and 220 g (11 moles) HF was heated at 140° for 8 hrs in a shaker tube. After distilling out residual HF, the tube contents were poured into excess ice-cold dilute NaOH. The product was extracted with methylene chloride, the extracts were passed through a short alumina column, and stripped to dryness. The residue was distilled in vacuo, collecting the cut boiling around 110°/1.7 Torr, which partly solidified on standing. It was stirred with methanol, filtered, washed with more methanol, and dried, yielding a total of 24.3 g (7%) of (XI) as white crystals in two crops 14.5 and 9.8 g) 9,9-Bis(trifluoromethyl)-2,7-dimethylxanthene (XI) is quite volatile, and sublimes in vacuo below 100°, and melts at 136°–137°. Analysis: Calc. for C$_{17}$H$_{12}$F$_6$O: C, 59.0; H, 3.47; F, 33.0; Found: C, 59.3; H, 3.56; F, 33.5%. The NMR spectrum was confirmatory: s 7.65, dd 7.23, d 7.06, s 2.35 ppm in 1:1:1:3 ratio.

EXAMPLE 8

9,9-Bis(trifluoromethyl)xanthene-2,7-dicarboxylic acid (XII)

To a refluxing solution of 34.6 g (0.1 mole) of 9,9-bis(trifluoromethyl)-2,7-dimethylxanthene (XI) in 400 ml pyridine and 100 ml water was added in portions 55 g (0.35 mole) potassium permanganate. After 90 min reflux (as the permanganate color was discharged, and $MnO_2$ precipitated) the mixture was filtered, and the filtrate was boiled down to about 100 ml. The residue was diluted with 70 g of 50% NaOH and 400 ml water, and oxidized with an additional 55 g $KMnO_4$ as above. Filtration of the mixture, and acidification with sulfuric acid yielded a white precipitate, which was filtered, and washed well with water. The material melts at 344°–347° in capillary (DSC shows a peak at 353°) and is sublimable in vacuo. Analysis: Calc. for $C_{17}H_8F_6O_5$: C, 50.3; H, 1.97; F, 28.1; Found: C, 51.2; H, 1.75; F, 25.8. IR: 1700 (vs), 1620, 1560 $cm^{-1}$.

EXAMPLE 9

9,9-Bis(trifluoromethyl)xanthene-2,7-dicarbonyl chloride (XIII)

A mixture of 20 g 9,9-bis(trifluoromethyl)xanthene-2,7-dicarboxylic acid (XII), 250 ml chloroform and 20 ml (excess) thionyl chloride was stirred and refluxed until the slurry became a pale yellow solution (4 hrs). The volatiles were distilled out, ultimately at house vacuum, and the residue (16 g, 73%) was purified by sublimation. The product (XIII) can also be recrystallized from toluene/heptane. M.p. 216°–218° IR: 1750 (vs) $cm^{-1}$. NMR: s 8.76, dd 8.31, d 7.44 in 1:1:1 ratio. Analysis: Calc. for $C_{17}H_6Cl_2F_6O_3$: C 46.1: H 1.35; Cl 16.0; F 25.7; Found: C 46.1; H 1.22; Cl 15.9; F 26.3.

EXAMPLE 10

9,9-Bis(trifluoromethyl)xanthene-2,7-diisocyanate (XIV)

A mixture of 4.43 g (0.01 mole) of 9,9-bis(trifluoromethyl)xanthene-2,7-dicarbonyl chloride (XIII), 4.43 g (0.07 mole) technical sodium azide and 100 ml toluene was refluxed overnight, the emanating nitrogen being measured by a wet-test meter. A total of 0.42 L (84% theory) was evolved. The mixture was filtered, and the filtrate evaporated, yielding 2.4 g (60%) of waxy solid, with a strong NCO band at 2270 $cm^{-1}$. It was sublimed in vacuo; m.p. 105°–107°.

EXAMPLE 11

9,9-Bis(trifluoromethyl)xanthene-2,7-diamine (XV)

A mixture of 10 g crude 9,9-bis(trifluoromethyl)-xanthene-2,7-dicarbonyl chloride (XIII) and 10 g sodium azide was stirred and refluxed overnight in 150 ml toluene. The mixture was filtered, and stripped to dryness, and the residue was refluxed for 3 hrs in 100 ml 20% hydrochloric acid. The slurry was filtered, and the filtrate was basified yielding some solid. The initial solid from the acid solution was stirred in excess aquomethanolic sodium hydroxide, and filtered. After drying, and combining the two solids, there was obtained 4.1 g (52%) of the diamine (XV). It can be distilled in a sublimation tube, and solidifies on cooling. After recrystallization from heptane, the product melted at 137°–138°, and had amine bands at 3470, 3400, 3370, 3350 and 3230 $cm^{-1}$. NMR: d (small J) 7.13, d (large J) 6.98, dd 6.80 and broad peak around 3.5 ppm in 1:1:!:2 ratio, corresponding to the 1, 3, 4, and amino protons, respectively.

EXAMPLE 12

9,9-Bis(trifluoromethyl)-3,6-dihydroxyxanthene (VIII)

A mixture of 300 g (2.7 moles) resorcinol, 225 g (1.35 moles) HFA and 300 g (15 moles) HF was heated in a shaker tube to 220° and kept there for 15 hrs. After distilling out excess HF, the reaction mixture was poured into a one-gallon polyethylene jar, half-filled with ice-water, and containing 200 g potassium acetate. The lumpy, and sometimes sticky, reddish-brown solid was isolated by filtration, washed with water, and air dried (yield of this crude solid averaged about 450 g). It was placed in a 4 L beaker, and the product was extracted with 2 L of boiling toluene, stirring well with a large metal spatula. The extracts were decanted hot from the red tar insoluble in toluene (but very soluble in acetone), and filtered through a 2-cm bed of Celite. On cooling, amber crystals of (VII) grew from the solution. They were filtered off, and a second crop was obtained by concentrating the mother liquors, and cooling. Total yield for a number of runs averaged about 100 g (20%). After repeated recrystallization from toluene, using Darco, pale yellowish platelets were obtained, m.p. 209°–210°. Analysis: Calc. for $C_{15}H_8F_6O_3$: C, 51.4; H, 2.29; F, 32.6; Found: C, 51.3; H, 2.45; F, 32.9%. The IR spectrum of (VII) has strong phenolic OH at 3100–3500 $cm^{-1}$, which disappears on acetylation (see below). NMR (in $(CD_3)_2CO$, since $CDCl_3$ solubility was very low): d 7.70; dd 6.65; OH singlet 5.42 ppm in 1:2:1 ratio.

Since neither chromatography, nor repeated recrystallization, using Darco, succeeded in removing the yellowish color, the diol was purified by conversion to the diacetate, which was purified by short-path distillation (main cut b.p. 195°–204°/1.4 Torr.). The diacetate was recrystallized from toluene/heptane yielding snow white crystals, and was then hydrolyzed by heating overnight in methanol with an equivalent amount of NaOH. The pale amber solution was stripped, the residue was stirred with 300 ml hot water, filtered, the solid was washed repeatedly with hot water and was then air-dried. Yield was quantitative.

EXAMPLE 13

9 9-Bis(trifluoromethyl)-3,6-bis(4-aminophenoxy)xanthene (VIII)

A mixture of 51.4 g of 9,9-bis(trifluoromethyl)-3,6-dihydroxyxanthene (VII) (0.147 mole), 46.3 g p-nitrochlorobenene (0.294 mole), 120 ml DMAC and 44.7 g anhydrous potassium carbonate (0.32 mole) was refluxed 4.5 hrs. The mixture was filtered, and the solid was washed with copious amounts of water, and then with methanol. After drying there was obtained a total of 83.7 g (96%) of crude product. The NMR spectrum of the dinitro compound was in agreement with the structure: the $A_2B_2$ pattern of the p-nitrophenoxy group as doublets at 8.28 and 7.18, d (b, large J) 7.92 (1-H), dd 6.94 (2-H) and d (small J) 6.87 (4-H ppm, in the correct 2:1:2:1:1 ratio.

The crude dinitro compound (75 g) was hydrogenated at 50° in 400 ml ethanol, using 3 g of 10% Pd/C catalyst at 500 psi hydrogen pressure, until there was no further pressure drop. The reduction mixture was filtered, the filtrate was concentrated down to 300 ml, cooled, and acidified with 280 ml of concentrated hydrochloric acid. The amine hydrochloride was filtered, washed with 20% hydrochloric acid, and dried under a nitrogen blanket. After drying in a vacuum oven, there was obtained 68 g of the dihydrochloride. It was dissolved in aqueous methanol, and the solution was made basic with sodium hydroxide, which liberated the diamine (XIII). It was isolated by filtration, and washed with much water. After drying under nitrogen, there was obtained 58 g of white solid. The material softens around 89°, and melts at 124° turning dark.

It was purified by distillation in vacuo, and boiled at 305°–307°/1.5 Torr. The NMR spectrum was confirmatory: $A_2B_2$ pattern as doublets at 8.27 and 7.18, the 4-H as broad d (large J) 7.92, 3-H as dd 6.94, 1-H as d (small J) 6.87, and $NH_2$ as broad (about 1.0 ppm) singlet, centered at 3.46 ppm, in the correct ratio: 2:2:1:1:2. Analysis: Calc. for $C_{27}H_{18}F_6O_3N_2$: C 60.9; H 3.38; F 21.4; N 5.26; Found: C 61.3; H 3.19; F 21.2; N 5.01%.

EXAMPLE 14

9-Phenyl-9-trifluoromethyl-2,3,6,7-tetramethylxanthene (XVI)

A mixture of 32 g (0.14 mole) of 3,3′-di-o-xylyl ether (DXE), 25 g (0.14 mole) trifluoroacetylbenzene, and 40 g (2 moles) HF was heated in a shaker tube at 140° for 8 hrs. After distilling off most of the HF, the residue was transferred to a polyethylene jar containing excess cold 20% NaOH. The product was extracted with methylene chloride, the extracts were run through a short column packed with alumina, and stripped to dryness. The pasty residue was stirred with methanol, and filtered. The resulting solid was washed with methanol, and air-dried. It was purified further by sublimation at 200°/1 Torr, and then by recrystallization from toluene. The product (XVI), obtained in 31 g (58%) yield, melted at 214°–215°. Analysis: Calc. for $C_{24}H_{21}F_3O$: C, 75.4; H, 5.50; F, 14.9; Found: C, 75.6; H, 5.52; F, 14.8%. NMR: d 7.40; quartet 7.30; s 6.96, s 6.58, s 2.23, s 2.07 ppm in the correct 2:3:2:2:6:6 ratio. Repeating this run on larger scale (200 g trifluoroacetylbenzene) and lower temperature (130°), improved the yield to 92%.

EXAMPLES 15 AND 16

9-Phenyl-9-(trifluoromethyl)xanthene-2,3,6,7-tetracarboxylic Acid (XVIII) and
9-Phenyl-9-(trifluoromethyl)xanthene-2,3,6,7-dianhydride (XVII)

A 75 g sample (0.196 mole) of 9-phenyl-9-trifluoromethyl-2,3,6,7-tetramethylxanthene (XVI) was oxidized with potassium permanganate in two stages, as was done before with (III). This yield of air-dried crude tetraacid (XVII) was 75 g (76%). The crude tetraacid (XVII) was converted to the dianhydride (XVII) heating under vacuum at 250°. The crude dianhydride (XVIII) can be sublimed in vacuo, and it also can be recrystallized from anisole, as a bis-solvate (by NMR: the PX peaks are at 7.89 and 7.60 ppm, in addition to anisole peaks). Purification of dianhydride (XVIII) was effected by high-precision sublimation in a McCarter sublimer. After a lower-melting foreshot, the main fraction was collected. It contained two different crystalline types: one consisted of clear light yellow crystals of dianhydride (XVIII) of 99.9% purity, m.p. 276°, the other component crystallized as opaque white clusters of needles. Purity of dianhydride (XVIII) was in the 98.1–99.0% range. Analysis: Calc. for $C_{24}H_9F_3O_7$: C: 61.8; H 1.93; F 12.2; Found: C 61.9, H 2.03, F 11.8.

EXAMPLE 17

9-Phenyl-9-pentafluoroethyl-2,3,6,7-tetramethylxanthene

A mixture of 101 g DXE and 100 g phenyl pentafluoroethyl ketone (both 0.45 mole) was heated with 112 g (5.6 mole) HF in a shaker tube at 130° for 8 hrs. After venting off excess HF, the reaction mixture was poured into excess cold aqueous sodium hydroxide. The product was extracted with a 50/50 mixture of methylene chloride and chloroform, the extracts were filtered through a 5-cm layer of alumina, and stripped. The residue was stirred with methanol, and was filtered. There was obtained 173 g (89.6%) of crude 9-phenyl-9-pentafluoroethyl-2,3,6,7-tetramethylxanthene. It was recrystallized from a 80/20 heptane/toluene mixture; m.p. 178°–179°. The IR spectrum was sharp, and the NMR spectrum consisted of: d 7.43, asym. m 7.23, s 6.91, s(b) 6.66, s 2.20 and s 2.04 in the correct 2:3:2:2:6:6 ratio. Analysis: Calc. $C_{25}H_{21}F_5O$: C 69.4; H 4.86; F 22.0; Found: C 69.5; H 4.92; F 22.5%.

EXAMPLE 18

9-Phenyl-9-perfluorooctyl-2,3,6,7-tetramethylxanthene

A mixture of 8.7 g of DXE and 20 g phenyl perfluorooctyl ketone (both 0.038 mole) was heated with 10 g (0.5 mole) HF in a shaker tube at 130° for 8 hrs. After venting excess HF, the product mixture was poured into excess cold aqueous alkali, and was extracted with a 50/50 mixture of methylene chloride and chloroform. The extracts were filtered through alumina, stripped and the residue was stirred with methanol. Filtration yielded 9-phenyl-9-perfluorooctyl-2,3,6,7-tetramethylxanthene in two crops, 6.9 and 1.1 g, for a total of 8.0 g (29% yield). The product was recrystallized from heptane; m.p. 177°–178°. NMR: d 7.41, m 7.28, s 6.94, s(b) 6.67, s 2.24, s 2.07, in the correct 2:3:2:2:6:6 ratio. Analysis Calc. for $C_{31}H_{21}F_{17}O$: C 50.8; H 2.87; F 44.1; Found: C 50.8; H 2.94; F 44.1%.

EXAMPLE 19

9-Phenyl-9-Perfluoropropyl-2,3,6,7-tetramethylxanthene

A mixture of 31 6 g phenyl perfluoropropyl ketone and 26 g DXE (both 0.115 mole) was heated with 30 g (1.5 moles) HF for 8 hrs at 135°. The reaction mixture was drowned in excess cold aqueous sodium hydroxide, extracted with a 50/50 methylene chloride and chloroform mixture; the extracts were filtered through alumina, stripped, and the residue was stirred with excess methanol. The white solid was filtered, and was obtained after drying in 24.9 g (44.9%) yield. After recrystallization from toluene/heptane, the product melted at 189°–190°. NMR: d 7.43, m 7.2–7.3, s 6.91, s(b) 6.66, s 2.23, s 2.07 in 2:3:2:2:6:6 ratio. Analysis: Calc. for $C_{26}H_{21}F_7O$: C 64.7; H 4.36; F 27.6; Found: C 64.7; H 4.55; F 25.0, 25.1.

EXAMPLE 20

9-Trifluoromethyl-9-pentafluoroethyl-2,3,6,7-tetramethylxanthene

A mixture Of 45.2 g DXE, 41 g trifluoromethyl pentafluoroethyl ketone (both 0.2 mole) and 50 g HF (2.5 moles) was heated in a shaker tube at 140° for 8 hrs. After venting residual HF, the reaction mixture was transferred to a polyethylene jar, containing ice-water, plus excess sodium hydroxide. The product was extracted with methylene chloride, the extracts were run through a bed of alumina, stripped, and the residue was stirred with methanol, and filtered. There was obtained a total of 18 g (21%) of white 9-trifluoromethyl-9-pentafluoroethyl-2,3,6,7-tetramethylxanthene. It is very soluble in toluene, chloroform, but insoluble in methanol. It was purified by sublimation, and then recrystallized from heptane; m.p. 139°–140°. The NMR spectrum was confirmatory: s (b) 7.57; s 6.93 and s 2.27 ppm in the correct 1:1:6 ratio. Analysis: Calc. for $C_{20}H_{16}F_8O$: C 56.6; H 3.77; F 35.85; Found: C.56.8; H 3.77; F 33.0, 33.1.

EXAMPLE 21

9-Phenyl-9-trifluoromethyl-2,7-dimethylxanthene (XIX)

A mixture of 114 g (0.54 mole) p-tolyl ether (X), 100 g (0.54 mole) trifluoromethyl phenyl ketone, and 160 g (8 moles) HF was heated in an autoclave for 8 hrs at 130°. After venting excess HF, the reaction mixture was quenched in 2 L ice water, containing 500 ml 50% NaOH. The product was extracted with methylene chloride, the extracts were filtered through a layer of alumina, stripped and distilled in vacuo. There was obtained 140 g (73%) of distillate boiling at 186°–210°/2 Torr. The solid was recrystallized from methanol or isopropyl alcohol. M.p. 150°–151°. NMR: d 7.40, m 7.30, s 7.07, s(b) 6.64, s 2.16 ppm in 2:3:4:2:6 ratio. Analysis: Calc. for $C_{22}H_{17}F_3O$: C 74.6; H 4.80; F 16.1; Found: C 74.7; H 4.90; F 15.9%.

EXAMPLE 22

9-Phenyl-9-trifluoromethylxanthene-2,7-dicarboxylic Acid (XX)

A 100 g batch of 9-phenyl-9-trifluoromethyl-2,7-dimethylxanthene (XIX) was oxidized in the same manner as a 75 g batch of (III). At the final filtration stage there was some granular white solid present in the $MnO_2$ filter cake. It was extracted with methylene chloride, and identified as unreacted starting material. Yield of recovered (XIX) was 16 g. From the filtrate, upon acidification with sulfuric acid there was obtained, after filtering, washing, and drying, 74 g (75%) of the dicarboxylic acid (XX). In another, larger scale preparation, the yield was 89%.

EXAMPLE 23

9-Phenyl-9-trifluoromethylxanthene-2,7-dicarbonyl Dichloride (XXI)

A slurry of 82 g (0.2 mole) of dried, crude 9-phenyl-9-trifluoromethylxanthene-2,7-dicarboxylic acid (XX) and 50 ml (large excess) of thionyl chloride in 500 ml chloroform was stirred and heated to gentle reflux in an oil bath. After 3 hrs of refluxing, the solution became clear. It was stirred overnight, and allowed to cool. Volatiles were stripped at atmospheric pressure, 400 ml heptane plus some Darco was added to the residue, the mixture was heated to reflux, and filtered through Celite. On cooling, crystals were obtained, which were filtered off and washed with hexane. 9-phenyl-9-trifluoromethylxanthene-2,7-dicarbonyl dichloride (XXI) was obtained in 64.7 g (71.7%) yield. Another 10.7 g (12%) of the dichloride was obtained by stripping the filtrate, and short-path distillation at about 200°/0.8 Torr, and stirring the syrupy distillate with heptane. After two recrystallizations from heptane the product melted at 128°–130°. IR: very strong carbonyl at 1750 $cm^{-1}$. NMR: dd 8.15, "s" 7.74, m 7.3–7.5 ppm in 2:2:7(5+2) ratio.

EXAMPLE 24

9-Phenyl-9-trifluoromethylxanthene-2,7-dicarbonyl azide

To a stirred solution of 5.0 g 9-phenyl-9-trifluoromethylxanthene-dicarbonyl dichloride (XXI) in 150 ml methylene chloride was added an aqueous solution of 5 g (large excess) sodium azide plus 0.05 g tetrabutylammonium bromide (as phase transfer agent). The two-phase mixture was stirred vigorously for 2 hrs, then the organic layer was separated, and filtered through a small bed of alumina. On evaporation, there was obtained 4.5 g of a white solid, which showed a strong azide band at 2140 $cm^{-1}$ and a strong carbonyl band at 1685 $cm^{-1}$. NMR: d 8.04, "s" 7.62, m 7.37, d 7.30 ppm in the correct 2:2:5:2 ratio. The compound melts with vigorous bubbling at 126°–127°.

EXAMPLE 25

9-Phenyl-9-trifluoromethylxanthene-2,7-diisocyanate (XXII)

A two phase system, consisting of 45 g (0.1 mole) of 9-phenyl-9-trifluoromethylxanthenedicarbonyl dichloride (XXI) in 300 ml methylene chloride, and 22 g sodium azide plus 0.5 g $Bu_4NBr$ in 100 ml water was stirred vigorously at room temperature for 1.5 hr. The orange organic layer was separated, stirred with Darco, and filtered through a Celite/alumina layer. The colorless filtrate was added dropwise to boiling toluene in a closed system, so that the solvent distilled out, and the nitrogen evolved could be measured by a wet-test meter. After all methylene chloride had distilled out and the toluene was refluxing, the theoretical amount of nitrogen was evolved. Toluene was distilled out at reduced pressure. The residue was extracted with 200 ml of boiling heptane. On cooling the solution, crystals were obtained in two crops 27.4 g and 7.8 g, for a total of 35.2 g (86.3%) of 9-phenyl-9-trifluoromethylxanthene-2,7-diisocyanate (XXII). The compound melts at 133°–134°, and contains a very strong NCO band at 2260 $cm^{-1}$. NMR: m 7.37, d 7.15, dd 7.06, "s" 6.56 ppm in 5:2:2:2 ratio. Analysis: Calc. for $C_{22}H_{11}F_3N_2O_3$: C 64.7; H 2.70; F 14.0; Found: C 64.9; H 2.91; F 13.8%.

EXAMPLE 26

9-(4-Perfluorohexylphenyl)-9-heptafluoropropyl-2,3,6,7-tetramethylxanthene

A mixture of 25.1 g dixylyl ether (0.11 mole) and 66 g 4-perfluorohexylphenyl heptafluoropropyl ketone (0.11 mole) was heated with 35 g (1.75 moles) HF in an autoclave at 140° C. for 8 hrs. After removal of excess HF the clave contents were transfered into a jar containing excess ice and sodium hydroxide. The product was extracted with methylene chloride, and the extracts were filtered through a bed of alumina, and stripped to dryness. The residue was stirred with methanol, and filtered yielding 60 g (68%) of the product in two crops (56.4 g, and 3.6 g). The material can be recrystallized from heptane or from isopropyl alcohol; M.p. 121°–122° C. It can also be distilled in vacuo. NMR: $A_2B_2$ doublet 7.55, s 6.95, s 6.58, s 2.23 and s 2.07 ppm in the correct 4:1:1:3:3 ratio.

EXAMPLE 27

9,9-Bis(trifluoromethyl)-3,6-dihydroxyxanthene polyester (IX)

A solution of 7.020 g of 9,9-bis(trifluoromethyl)-3,6-dihydroxyxanthene (VII) and 6.5 ml of triethylamine in 50 ml of methylene chloride was stirred at room temperature as 4.070 g of a 70:30 mixture of isophthaloyl chloride and terephthaloyl chloride in 20 ml of methylene chloride was added over 5 min. The mixture became cloudy and was stirred at reflux for one hour, and then at room temperature overnight. The solution was added to 500 ml of methanol in a blender; the precipitated polymer was filtered, reblended with 500 ml of fresh methanol, and filtered again. The polymer was then blended with warm tap water, filtered, washed with methanol and dried to yield 9.2 g of polyester; u inh=0.37 (0.4% in NMP). Film was cast from a 15% solution of polymer in THF and the solvent was removed in a vacuum oven at 130°. The film was tested for oxygen and nitrogen separation at 500 psig (feed gas: 21% $O_2$/79% $N_2$): the $O_2/N_2$ separation factor was 4.50 and the oxygen permeability was 7.0 Barrers. The film was fairly strong even at this low molecular weight.

I claim:

1. A polyimide polymer having the following recurring structural unit

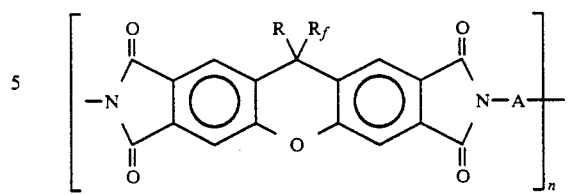

wherein R is selected from the group consisting of phenyl, substituted phenyl and perfluoroalkyl of 1 to 16 carbon atoms; $R_f$ is perfluoroalkyl of 1 to 16 carbon atoms; A is a divalent radical of a diamine containing at least two carbon atoms, the two amino groups of said diamine each being attached to separate carbon atoms of said divalent radical; and n is a positive integer.

2. The polyimide polymer of claim 1 wherein R is $CF_3$ and $R_f$ is $CF_3$.

3. The polyimide polymer of claim 1 wherein R is phenyl and $R_f$ is $CF_3$.

4. The polyimide polymer of claim 1 wherein the diamine is 4,4'-diaminodiphenyl ether.

5. The polyimide polymer of claim 2 wherein the diamine is 3,4'-diaminodiphenyl ether.

6. The polyimide polymer of claim 2 wherein the diamine is paraphenylene diamine.

7. The polyimide polymer of claim 2 wherein the diamine is resorcinol oxydianiline.

8. The polyimide polymer of claim 2 wherein the diamine is a blend of 4,4'-diaminodiphenyl ether and paraphenylene diamine.

* * * * *